(12) United States Patent
Bonitatibus, Jr. et al.

(10) Patent No.: US 9,149,545 B2
(45) Date of Patent: Oct. 6, 2015

(54) NANOPARTICLE-BASED IMAGING AGENTS FOR X-RAY/COMPUTED TOMOGRAPHY AND METHODS FOR MAKING SAME

(75) Inventors: Peter John Bonitatibus, Jr., Saratoga Springs, NY (US); David Cheney deMoulpied, New Baltimore, NY (US); Andrew Soliz Torres, Troy, NY (US); Amit Mohan Kulkarni, Clifton Park, NY (US); Robert Edgar Colborn, Niskayuna, NY (US); Paul William Buckley, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 999 days.

(21) Appl. No.: 12/276,817

(22) Filed: Nov. 24, 2008

(65) Prior Publication Data

US 2009/0087383 A1 Apr. 2, 2009

Related U.S. Application Data

(63) Continuation-in-part of application No. 11/627,529, filed on Jan. 26, 2007, which is a continuation-in-part of application No. 11/265,728, filed on Nov. 2, 2005, now abandoned.

(51) Int. Cl.
| | |
|---|---|
| A61K 49/04 | (2006.01) |
| B82Y 30/00 | (2011.01) |
| C01G 27/02 | (2006.01) |
| C01G 35/00 | (2006.01) |
| C01G 3/12 | (2006.01) |
| B82Y 5/00 | (2011.01) |
| C09C 3/12 | (2006.01) |

(52) U.S. Cl.
CPC ............... *A61K 49/0423* (2013.01); *B82Y 5/00* (2013.01); *B82Y 30/00* (2013.01); *C01G 27/02* (2013.01); *C01G 35/00* (2013.01); *C09C 3/12* (2013.01); *C01P 2004/04* (2013.01); *C01P 2004/64* (2013.01)

(58) Field of Classification Search
CPC ..... A61K 49/0423; A61K 49/04; B82Y 5/00; B82Y 30/00; C09C 3/12; C01G 35/00; C01P 2004/64
USPC .......................................... 424/9.4, 9.41, 9.42
See application file for complete search history.

(56) References Cited

U.S. PATENT DOCUMENTS

| | | | |
|---|---|---|---|
| 4,079,124 A | 3/1978 | Winchell | |
| 4,827,945 A * | 5/1989 | Groman et al. | 424/9.32 |
| 4,863,715 A | 9/1989 | Jacobsen et al. | |
| 5,458,869 A | 10/1995 | Berg et al. | |
| 5,580,492 A | 12/1996 | Bonnemann et al. | |
| 5,614,168 A | 3/1997 | Berg et al. | |
| 5,618,514 A | 4/1997 | Schröder et al. | |
| 5,665,331 A | 9/1997 | Bagchi et al. | |
| 5,695,480 A | 12/1997 | Evans et al. | |
| 5,851,508 A | 12/1998 | Greff et al. | |
| 5,916,539 A | 6/1999 | Pilgrimm | |
| 5,928,626 A | 7/1999 | Klaveness et al. | |
| 6,121,425 A | 9/2000 | Hainfeld et al. | |
| 6,123,920 A * | 9/2000 | Gunther et al. | 424/9.322 |
| 6,203,778 B1 | 3/2001 | Brasch | |
| 6,369,206 B1 | 4/2002 | Leone et al. | |
| 6,417,244 B1 | 7/2002 | Wellinghoff et al. | |
| 6,645,464 B1 | 11/2003 | Hainfeld | |
| 6,660,248 B2 | 12/2003 | Wilson et al. | |
| 6,743,936 B1 | 6/2004 | Wellinghoff et al. | |
| 6,818,199 B1 | 11/2004 | Hainfeld et al. | |
| 6,955,639 B2 | 10/2005 | Hainfeld et al. | |
| 6,995,639 B2 | 2/2006 | Minowa et al. | |
| 7,037,583 B2 * | 5/2006 | Furman et al. | 428/403 |
| 7,575,621 B2 * | 8/2009 | Vanheusden et al. | 75/351 |
| 2003/0158289 A1 | 8/2003 | Rusin et al. | |
| 2003/0199653 A1 | 10/2003 | McCormick, III et al. | |
| 2004/0029996 A1 | 2/2004 | Kuhn | |
| 2005/0020869 A1 | 1/2005 | Hainfeld et al. | |
| 2006/0084278 A1 | 4/2006 | Winter et al. | |

FOREIGN PATENT DOCUMENTS

| | | |
|---|---|---|
| EP | 1430913 A1 | 6/2004 |
| EP | 1425245 B1 | 6/2010 |
| JP | 08508721 A | 9/1996 |

(Continued)

OTHER PUBLICATIONS

Chan, D. et al., Dental Materials, 1999, 15, pp. 219-222.*

(Continued)

*Primary Examiner* — Michael G Hartley
*Assistant Examiner* — Leah Schlientz
(74) *Attorney, Agent, or Firm* — Eileen B. Gallagher

(57) ABSTRACT

The present invention is generally directed to core/shell nanoparticles, wherein such core/shell nanoparticles comprise a nanoparticle core and a nanoshell disposed about the nanoparticle core such that, in the aggregate, they form a core/shell nanoparticle that is operable for use as an imaging agent in X-ray/computed tomography (CT). Typically, such core/shell nanoparticle-based X-ray CT imaging agents further comprise a targeting species for targeting the imaging agent to diseased sites. Included herein are methods for forming such agents, comprising forming an ensemble of core/shell nanoparticles, wherein the mean diameter of the ensemble of core/shell nanoparticles is selected so as to render the nanoparticles in the ensemble substantially clearable by a mammalian kidney.

8 Claims, 5 Drawing Sheets

(56) References Cited

FOREIGN PATENT DOCUMENTS

| | | |
|---|---|---|
| JP | 2005500436 A | 1/2005 |
| WO | WO9847532 A1 | 10/1998 |
| WO | WO0006244 A2 | 2/2000 |
| WO | WO0003890 A1 | 6/2000 |
| WO | WO03075961 A2 | 9/2003 |
| WO | WO2004112590 A2 | 12/2004 |
| WO | WO2005046733 A1 | 5/2005 |
| WO | WO2005051435 A2 | 6/2005 |
| WO | WO2005058360 A2 | 6/2005 |
| WO | WO2005070473 A1 | 8/2005 |
| WO | WO2006025267 A1 | 3/2006 |
| WO | WO2006054240 A2 | 5/2006 |

OTHER PUBLICATIONS

Furman et al., Critical Reviews in Biomedical Engineering, 2000, 28, p. 439-443.*

Sweeney et al., "Rapid Purification and Size Separation of Gold Nanoparticles via Diafiltration", JACS Articles, J. Am. Chem. Soc., vol. 128, pp. 3190-3197, 2006.

Yu et al., "Metal-Based X-Ray Contrast Media", American Chemical Society, Chem. Rev. vol. 99, pp. 2353-2377, 1999.

Leike et al., "Characterization of Continuously Extruded Iopromide-Carrying Liposomes for Computed Tomography Blood-Pool Imaging", Investigative Radiology, vol. 36, No. 6, pp. 303-308, 2001.

Yordanov et al., "Novel Iodinated Dendritic Nanoparticles for Computed Tomography (CT) Imaging", American Chemical Society, Nano Letters, vol. 2, No. 6, pp. 595-599, 2002.

Beutel et al., Handbook of Medical Imaging, "X-Ray Production, Interaction and Detection", Progress in Medical Physics and Psychophysics, vol. 1, pp. 32-33, 2000.

Hermanson, "Bioconjugate Techniques", Pierce Chemical Company, Rockford, Illinois, Chapter 2, pp. 136-166, 1996.

Ribeiro et al., "Low Optical Loss Planar Waveguides Prepared in an Organic-Inorganic Hybrid System", Applied Physics Letters, vol. 77, No. 22, pp. 3502-3504, Nov. 27, 2000.

Engler et al., "Review of Dual-Energy Computed Tomography Techniques", The American Society for Nondestructive Testing, Inc., Materials Evaluation, vol. 48, pp. 623-629, May 1990.

Braune et al., "Tantalum Oxide Nanomers for Optical Applications", SPIE Conference on Organic-Inorganic Hybrid Materials for Photonics, San Diego, California, SPIE vol. 3469, pp. 124-132, Jul. 1998.

Parraud et al., "Stabilization and Characterization of Nanosized Niobium and Tantalum Oxide Sols—Optical Applications for High-Power Lasers", J. Am. Ceram. Soc., vol. 75, No. 8, pp. 2289-2292, 1992.

Li et al., "A Novel Simple Route to Synthesize Aqueous Niobium and Tantalum Precursors for Ferroelectric and Photocatalytic Applications", Mater. Res. Soc. Symp. Proc., vol. 492, 7 pages, 2006.

Tomita et al., "A Water-Soluble Titanium Complex for the Selective Synthesis of Nanocrystalline Brookite, Rutile, and Anatase by a Hydrothermal Method", Angew. Chem. Int. Ed., vol. 45, Communications, pp. 2378-2381, 2006.

Sun et al., "Sol-Gel Chemistry of Tantala HR Coatings: Structure and Laser-Damage Resistance", Journal of Sol-Gel and Technology, vol. 8, pp. 493-497, 1997.

Ozer et al., "Structural and Optical Properties of Sol-Gel Deposited Proton Conducting Ta2O5 Films", Journal of Sol-Gel Science and Technology, vol. 8, pp. 703-709, 1997.

Romero et al., Synthesis of Ta2O5 Nanorods in the Presence of Poly L-Lysine by a Sol-Gel Process, Annali de Chimica, vol. 95, pp. 703-707, 2005.

Bönnemann et al., "Nanoscopic Metal Particles—Synthetic Methods and Potential Applications", Eur. J. Inorg. Chem., Microreview, pp. 2455-2480, 2001.

Monreal et al., "Synthesis of Nanoparticles of Tantalum (V) Oxide in Presence of D-Galactose, 3,6 Anhydro-L-Galactose", Int. J. Materials and Product Technology, vol. 27, Nos. 1/2, pp. 80-84, 2006.

Fang et al., "Surface Sol-Gel Synthesis of Ultrathin Titanium and Tantalum Oxide Films", Journal of Nanoparticle Research, vol. 1, pp. 43-49, 1999.

Kominami et al., "Solvothermal Synthesis of Tantalum (V) Oxide Nanoparticles and Their Photocatalytic Activities in Aqueous Suspension Systems", Phys. Chem. Chem. Phys., vol. 3, pp. 2697-2703, 2001.

* cited by examiner

NANOPARTICLE-BASED IMAGING AGENTS FOR X-RAY/COMPUTED TOMOGRAPHY AND METHODS FOR MAKING SAME

RELATED APPLICATIONS

This application is a continuation-in-part of U.S. patent application Ser. No. 11/627,529, filed Jan. 26, 2007, which itself is a continuation-in-part of U.S. patent application Ser. No. 11/265,728, filed Nov. 2, 2005, entitled "Nanoparticle-based Imaging Agents for X-Ray/Computer Tomography," each of which is hereby incorporated herein by reference.

TECHNICAL FIELD

The present invention relates generally to imaging agents for use in X-ray/computed tomography, and more specifically to nanoparticle-based imaging agents and methods for making same.

BACKGROUND INFORMATION

Iodinated benzoic acid derivatives continue to serve as standard X-ray/computed tomography (CT) imaging agents, despite the risk factors and side effects associated with intravenous iodine injection. Additionally, such standard CT imaging agents are typically of low molecular weight, and they are known to clear from the human body very rapidly, making it difficult to target these agents to disease sites (Shi-Bao Yu and Alan D. Watson, Chem. Rev. 1999, 99, 2353-2377).

The literature describes experimental nanoparticle systems containing gadolinium (Gd) or iodine (I) for CT imaging. However, in such systems, only a relatively small number of heavy atoms may be delivered to/in the vicinity of the target tissues. Such approaches include a liposomal approach, in which iodinated molecules are encapsulated into liposomes (Leike et al., Invest. Radiol. 2001, 36(6), 303-308), as well as a dendritic approach, in which iodine atoms are conjugated to G-4 Starburst® polyamidoamide (PAMAM) dendrimers (Yordanov et al., Nano Letters 2002, 2(6), 595-599). Both approaches deliver, at most, a couple hundred heavy metal (i.e., gadolinium) atoms.

Efforts to deliver a greater number of heavy metal atoms have included the use of nanoparticles of such heavy metals. See PCT International Publication Nos. WO 03/075961 A2 and WO 2005/051435 A2. Although nanoparticles of elemental (zerovalent) metal species have the highest density (number of heavy metal atoms/volume), they suffer from issues such as robust synthesis and instability due to oxidation. Nanoparticles of inert metals such as gold (e.g., such as described in WO 03/075961 A2) can overcome these issues, but are not very cost effective.

As a result of the foregoing, there is a continuing need for new imaging agents for CT, especially to the extent that such imaging agents can provide for improved performance and benefit in one or more of the following areas: robust synthesis, reduced cost, image contrast enhancement, increased blood half-life, decreased toxicity, decreased radiation dose, and targeting capability.

BRIEF DESCRIPTION OF THE INVENTION

The present invention is generally directed to core/shell nanoparticles, wherein such core/shell nanoparticles comprise a nanoparticle core and a nanoshell disposed about the nanoparticle core such that, in the aggregate, they form a core/shell nanoparticle that is operable for use as an imaging agent in X-ray/computed tomography.

In some embodiments, the present invention is directed to an imaging agent comprising an active nanoparticle core comprising at least one heavy metal element in a non-zero valent state, and a passive nanoshell, the nanoshell being disposed about the nanoparticle core such that in the aggregate they form a core/shell nanoparticle that is operable for use as an imaging agent in CT imaging.

In some embodiments, an X-ray/computed tomography imaging solution comprises an ensemble of the imaging agents according to any of the embodiments described herein, wherein the mean diameter of the ensemble is not more than about 10 nm.

In some embodiments, the present invention is directed to methods of making any of the above-described imaging agents. In some or other embodiments, the present invention is directed to methods of using such imaging agents in CT.

In some embodiments, the present invention is directed to methods for making a preparation for use in imaging via X-ray/computed tomography. The method comprises forming an ensemble of core/shell nanoparticles, wherein the forming step comprises
  a) providing a first precursor material comprising a heavy metal element;
  b) forming an active core from the first precursor material, the core comprising the heavy metal element in a non-zero valent state;
  c) providing a second precursor material; and
  d) forming a passive shell from the second precursor material, wherein the passive shell is disposed about the core such that the core and the shell form a core/shell nanoparticle;
wherein the mean diameter of the ensemble of core/shell nanoparticles is selected so as to render the nanoparticles in the ensemble substantially clearable by a mammalian kidney.

The present invention uses a nanoparticle approach to deliver a relatively large number of high-density, highly-attenuating (radio-opaque molecular structures with effective atomic number greater than or equal to Z=34, the atomic number of selenium) atoms in elemental or molecular form to improve CT contrast enhancement. In some embodiments, the present invention provides for targeting of specific disease sites by the CT imaging agent. In some embodiments, the present invention provides for macrophage uptake of the CT imaging agent. In some embodiments, the present invention provides for a CT imaging agent with increased blood half-life.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

Figure 1:
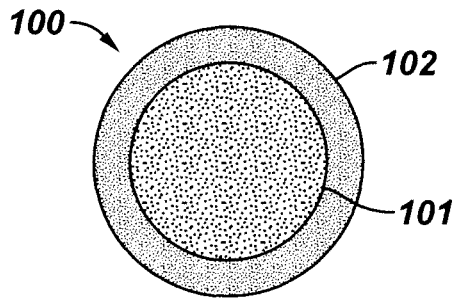
FIG. 1 generally depicts a cross-sectional view of a core/shell nanoparticle so as to illustrate the relationship between the components.

The present invention is generally directed to core/shell nanoparticles, wherein such core/shell nanoparticles comprise a nanoparticle core and a nanoshell disposed about the nanoparticle core such that, in the aggregate, they form a core/shell nanoparticle that is operable for use as an X-ray imaging agent, particularly in CT.

Referring to the drawings in general, it will be understood that the illustrations are for the purpose of describing a particular embodiment of the invention and are not intended to limit the invention thereto.

While most of the terms used herein will be recognizable to those of skill in the art, the following definitions are nevertheless put forth to aid in the understanding of the present invention. It should be understood, however, that when not explicitly defined, terms should be interpreted as adopting a meaning presently accepted by those of skill in the art.

"Computed Tomography," abbreviated "CT," as defined herein and also known as computed axial tomography or computer-assisted tomography (CAT) and body section roentgenography, is a medical imaging method employing tomography where digital processing is used to generate a three-dimensional image of the internals of an object (or subject) from a large series of two-dimensional X-ray images taken around a single axis of rotation. While the discussion herein focuses on computed tomography, it will be appreciated by those of skill in the art that such discussions apply generally to all types of X-ray imaging.

"Imaging agents," as defined herein and also known as contrast agents, are agents that comprise a material that can significantly attenuate incident X-ray radiation causing a reduction of the radiation transmitted through the volume of interest. After undergoing CT image reconstruction and typical post-processing, this increased X-ray attenuation is interpreted as an increase in the density of the volume of interest, which creates a contrast enhancement in the volume comprising the contrast agent relative to the background tissue in the image. Because the discussion herein is generally applicable to all forms of X-ray imaging, the imaging agents of the present invention are generally referred to herein as "X-ray/computed tomography imaging agents." This term is used interchangeably with "computed tomography (CT) agents."

In reference to the core and shell components of a core/shell nanoparticle, the terms "active" and "passive" refer to the components' ability to create a contrast enhancement in CT imaging. A conventional CT scanner scans uses a broad spectrum of X-ray energy between about 10 keV and about 140 keV. Those skilled in the art will recognize that the amount of X-ray attenuation passing through of a particular material per unit length is expressed as the linear attenuation coefficient. At an X-ray energy spectrum typical in CT imaging, the attenuation of materials is dominated by the photo-electric absorption effect and the Compton Scattering effect. Furthermore, the linear attenuation coefficient is well known to be a function of the energy of the incident X-ray, the density of the material (related to molar concentration), and the atomic number (Z) of the material. For molecular compounds or mixtures of different atoms the 'effective atomic number,' $Z_{eff}$, can be calculated as a function of the atomic number of the constituent elements. The effective atomic number of a compound of known chemical formula is determined from the relationship:

$$Z_{eff} = \left[ \sum_{k=1}^{P} w_{f_k} Z_k^{\beta} \right]^{\frac{1}{\beta}} \quad \text{(Eq. 1)}$$

where $Z_k$ is the atomic number of simple elements, P is the total quantity of simple elements, and $w_{f_k}$ is the weight fraction of simple elements with respect to the total molecular weight of the molecule (related to the molar concentration). The optimal choice of the incident X-ray energy for CT imaging is a function of the size of the object to be imaged and is not expected to vary much from the nominal values. It is also well known that the linear attenuation coefficient of the contrast agent material is linearly dependent on the density of the material, i.e., the linear attenuation coefficient can be increased if the material density is increased or if the molar concentration of the contrast material is increased. However, the practical aspects of injecting contrast agent material into patients, and the associated toxicity effects, limit the molar concentration that can be achieved. Therefore, it is reasonable to separate potential contrast agent materials according to their effective atomic number. Based on simulations of the CT contrast enhancement of typical materials for a typical CT energy spectrum with a molar concentration of approximately 50 mM, it is estimated that materials with effective atomic number greater than or equal to 34 will yield appropriate contrast enhancement of about 30 Hounsfield units (HU), or 3% higher contrast than water. Therefore, we have defined potential CT contrast materials as being either passive, having an effective atomic number of less than 34 (i.e., $Z_{eff}$<34), or active, having an effective atomic number greater than or equal to 34 (i.e., $Z_{eff}$≥34). See, e.g., Chapter 1 in Handbook of Medical Imaging, Volume 1, Physics and Psychophysics, Eds. J. Beutel, H. L. Kundel, R. L. Van Metter, SPIE Press, 2000).

A "nanoparticle," as defined herein, is a particle with an average diameter of between about 1 nm and about 500 nm, and can be used to refer to nanoparticle cores and core/shell nanoparticle aggregates. Such nanoparticles can be spherical or irregularly shaped, and, particularly on the smaller end of this size range, are differentiated from molecular complexes. A "nanoshell," as defined herein, is the shell region of the core/shell nanoparticle. Such a nanoshell is disposed about the nanoparticle core in such a way that it may or may not conform to the topography of the underlying nanoparticle core.

As mentioned above, and referring to FIG. 1, in some embodiments the present invention is directed toward an imaging agent comprising: (a) a nanoparticle core 101; and (b) a nanoshell 102, the nanoshell being disposed about the nanoparticle core such that, in the aggregate, they form a core/shell nanoparticle 100 that is operable for use as an imaging agent in computed tomography (generally, X-ray) imaging. While FIG. 1 depicts a cross-section of a perfectly spherical core/shell nanoparticle, such core/shell nanoparticles can also be irregularly-shaped.

In some embodiments, the above-described imaging agent further comprises at least one targeting agent. Such targeting agents are useful for targeting the imaging agents to specific diseased regions of a subject's body. Typically, the targeting agent is an antibody (e.g., IgG) or other peptide, but can also be a nucleic acid (e.g., DNA, RNA) or other suitable chemical species. Generally, the targeting agent is attached to one or both of the nanoparticle core and the nanoshell disposed about the nanoparticle core. Such attachment typically comprises a linkage such as, but not limited to, a peptide linkage, a disulfide linkage, an isothiourea linkage, an isourea linkage, a sulfonamide linkage, an amine linkage, a carbamate linkage, an amidine linkage, a phosphoramidate linkage, a thioether linkage, an arylamine linkage, an aryl thioether linkage, an ether linkage, a hydrazone linkage, a triazole linkage, an oxime linkage, and combinations thereof. See, e.g., Chapter 2 in Bioconjugate Techniques. G. T. Hermanson, Academic Press, 1996.

In some embodiments, the above-described CT imaging agents are optimized for macrophage uptake via control of the core/shell nanoparticle surface charge and/or the presentation of functional groups which induce macrophage uptake (e.g., polyvinyl sulfate).

For the core/shell nanoparticles described herein for use as imaging/contrast agents in CT, the nanoparticle core typically has an average diameter of from about 1 nm to about 100 nm, more typically from about 2 nm to about 80 nm, and most typically from about 2 nm to about 20 nm. The nanoshell disposed about the nanoparticle core typically has an average thickness of from about 0.5 nm to about 100 nm. Accordingly, the aggregate of the nanoparticle core and the nanoshell of the imaging agent typically has an average diameter of from about 2 nm to about 500 nm, more typically from about 2 nm to about 100 nm, and most typically from about 3 nm to about 20 nm.

It will be understood that it may be desirable for the aggregate of the nanoparticle core and the nanoshell to be excretable by a mammalian kidney, typically a human kidney. Accordingly, the aggregate of the nanoparticle core and the nanoshell of the imaging agent may have an average diameter of from about 1 to about 20 nm, more typically from about 2 to about 12 nm, and most typically from about 3 nm to about 8 nm.

In some embodiments, an X-ray/computed tomography imaging solution comprises an ensemble of the imaging agents of according to any of the embodiments described herein, wherein the mean diameter of the ensemble is not more than about 10 nm, more typically not more than about 7 nm, most typically not more than about 6 nm.

Active Core/Passive Shell Nanoparticles

Figure 2:
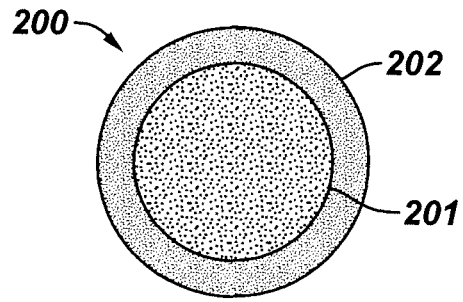
FIG. 2 depicts a cross-sectional view of a core/shell nanoparticle comprising an active core and a passive shell, in accordance with some embodiments of the present invention.

Referring to FIG. 2, in some embodiments, the present invention is directed to an imaging agent 200 comprising an active nanoparticle core 201 and a passive nanoshell 202, the nanoshell being disposed about the nanoparticle core such that in the aggregate they form a core/shell nanoparticle 200 that is operable for use as an imaging agent in CT imaging.

The material of which the above-described nanoparticle core 201 is comprised is generally limited only in that it comprises an active material for contrast enhancement in CT ($Z_{eff}$≥34), where the active material comprises at least one heavy metal element in a non-zero valent state. Generally, the nanoparticle core comprises a material distinguishable from that of the nanoshell. The nanoparticle core typically comprises material such as, but not limited to, metal oxides.

It will be understood, that such active materials may comprise elements of high atomic weight (e.g., heavy metals). That is, suitable metals include, but are not limited to, heavy metals. Suitable heavy metals include, but are not limited to, gadolinium (Gd), samarium (Sm), neodymium (Nd), tungsten (W), tantalum (Ta), bismuth (Bi), hafnium (Hf), barium (Ba), dysprosium (Dy), and combinations thereof. Thus, the nanoparticle core may comprise material such as, but not limited to, a compound of a heavy metal, where suitable compounds include, but are not limited to, oxides. Suitable oxides include, but are not limited to, tungsten oxide, tantalum oxide, hafnium oxide, bismuth oxide, and combinations thereof. By way of example and not limitation, the effective atomic number, $Z_{eff}$, for $Ta_2O_5$ is about 69.

The material of which the nanoshell 202 is comprised is not particularly limited, but generally does not comprise active CT contrast agent material ($Z_{eff}$<34) and must generally be capable of being disposed about the nanoparticle core. Suitable such materials include, but are not limited to, ligands, oligomers, polymers, clusters, carbohydrate species, functionalized silica, and combinations thereof. For example, suitable shell materials include, but are not limited to, polyethylene glycol, polyethylene imine, polymethacrylate, polyvinylsulfate, polyvinylpyrrolidinone, citrate, malate, glycolate, silanes, and combinations thereof.

According to some embodiments, the material of which the nanoshell is made is water soluble. Alternatively or in combination, according to some embodiments, the material of which the nanoshell is made is biocompatible.

Methods of Making

In some embodiments, the present invention is directed to method of making any or all of the above-described types of imaging agents in CT applications.

For example, when the imaging agent comprises an active nanoparticle core and a passive nanoshell, such methods may comprise the steps of: (a) providing a first precursor material comprising a heavy metal element; (b) forming an active core from the first precursor material, the active core comprising the heavy metal element in a non-zero valent state; (c) providing a second precursor material; and (d) forming a passive shell from the second precursor material, wherein the passive shell is disposed about the core such that the core and the shell form a core/shell nanoparticle. In some embodiments, the passive shell comprises a water soluble material derived from the second precursor material. Alternatively, or in combination, in some embodiments, the method further comprises controlling the average diameter of the nanoparticle.

It will be understood that the order and/or combination of steps may be varied. Thus, according to some embodiments, steps (a), (b), (c), and (d) occur as sequential steps so as to form the nanoparticle from the active core and the second precursor. By way of example and not limitation, in some embodiments, the first precursor comprises the heavy metal in a non-zero valent state; wherein the core comprises an oxide of the heavy metal in the same non-zero valent state; and wherein step (b) comprises hydrolysis of the first precursor. According to some embodiments, the first precursor is a salt, such as an alkoxide or halide, of the heavy metal, and the hydrolysis proceeds upon combining the first precursor, an acid, water, or water analog such as deuterium oxide, in an alcoholic solvent. The water, or water analog, initiates the hydrolysis. The molar ratio of the acid to the heavy metal may be selected so as to control the size of the nanoparticle core. According to some embodiments, when the core comprises an oxide of a heavy metal, a silicon-containing material is attached to the core via Si—O linkages. According to some embodiments, the siloxane includes, but is not limited to polymerizable groups. The polymerization may proceed via acid induced condensation polymerization. Alternatively, according to some embodiments, a polymer may be physisorbed on the core. According to any of the above-described embodiments, the polymer may be water soluble and biocompatible. Suitable polymers include, but are not limited to polyethylene glycol (PEG), polyethylene imine (PEI), polymethacrylate, polyvinylsulfate, polyvinylpyrrolidinone and combinations thereof. It will be understood that we contemplate equivalent methods for forming nanoparticles comprising non-zero valent metallic cores comprising alternative heavy metal compounds described herein. By way of example and not limitation, the above description has been used to form niobium oxide nanoparticles starting from niobium ethoxide, $Nb(OEt)_5$.

Alternatively, according to some embodiments, steps (a) and (c) occur together such that steps (b) and (d) occur together so as to form the nanoparticle directly from the first and second precursors. By way of example and not limitation, according to some embodiments, the first precursor comprises the heavy metal in a zero valent state; wherein the core comprises an oxide of the metal; and wherein and steps (b) and (d) together comprise adding the first and second precursors to a basic aqueous solution. According to some embodiments, the basic solution has a pH of at least about 9. Direct formation of the core and shell in the same step, such as by combining steps (a) and (b) is an unexpected discovery. Further, we have surprisingly discovered that exchange reactions which are well known for metal nanoparticles, such as those involving citrate shell formation on gold nanoparticles, may be used for making ligand based shells disposed about non-metallic cores, using, for example, the present direct preparation. When the shell comprises a ligand, the first precursor may comprise a ligand reagent. For example, when the ligand is a carboxylic acid anion, such as citrate, the ligand reagent is the associated carboxylic acid. Suitable alternative ligand reagents include, but are not limited to, sugars, alcohols, polyaldehydes, and combinations thereof. Glucose is an example that allows for the preparation of very small nanoparticles. Other suitable reagents include, but are not limited to, glycolic acid and malic acid. According to some embodiments, the diameter of the nanoparticles is controlled via selection of the identity and/or amount of ligand.

In combination with any of the above-described embodiments, in some embodiments, a method of making a X-ray/computed tomography preparation (e.g. containing a plurality of imaging agents) comprises forming an ensemble of core/shell nanoparticles, wherein the mean diameter of the ensemble is not more than about 10 nm, more typically not more than about 7 nm, most typically not more than about 6 nm; in some embodiments the mean diameter is not more than about 3 nm. It will be understood that according to some embodiments, the mean diameter is selected so as to render the nanoparticles in the ensemble substantially clearable by a mammalian kidney, such as a human kidney, in particulate form.

The mean diameter of the ensemble can be controlled using any technique suitable for controlling the size distribution of nanoparticles in solution. Accordingly, in some embodiments, forming the ensemble described above includes a fractionation step, wherein a raw ensemble in solution is passed through a process that divides the raw ensemble into at least two populations having different particle size. Of course, careful process design and control is desirable for the synthesis of the nanoparticles to generate a population of particles having a very narrow size distribution, so that any subsequent fractionation step does not dramatically reduce overall process yield by removing a large fraction of undesirably sized material. Several suitable fractionation techniques are known in the art, including, for instance, various filtration processes. Normal filtration, where a particle-containing fluid is forced directly toward a filter membrane under an applied pressure (as created by, for example, centrifugal force or other means), is a common technique. Another suitable technique is tangential flow filtration, where the fluid is pumped tangentially along the surface of the membrane with an applied pressure that serves to force a portion of the fluid through the membrane. In this technique, unlike in normal filtration, the retained, larger particles are swept along by the tangential flow, rather than accumulating at the surface of the membrane. This sweeping effect is often advantageous in achieving efficient size-based separation of very fine particulate ensembles. Another example of a suitable technique is diafiltration, a type of tangential flow filtration process in which buffer is added to the process stream as filtrate is removed. One skilled in the art is familiar with these processes and how to use them to obtain a desired size distribution for a nanoparticle ensemble. In some embodiments, the raw nanoparticle ensemble is fractionated to provide a product ensemble of nanoparticles having mean diameter in accordance with any of the ranges given above.

In some embodiments, the X-ray/computed tomography preparation is purified to remove undesirable species that may interfere with or otherwise degrade the performance of the preparation. Techniques such as dialysis are suitable for this purpose. Moreover, techniques such as diafiltration have been shown to effectively purify and fractionate nanoparticle solutions in one processing step. See, for example, Sweeney et al., J. Am. Chem. Soc. 2006, vol. 128, pp 3190-3197.

Methods of Using

Figure 3:
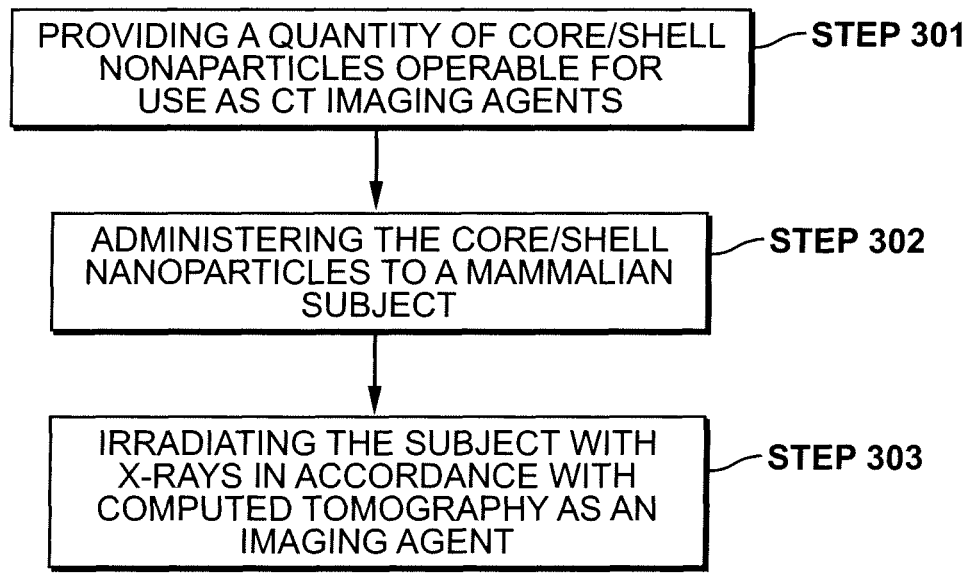
FIG. 3 illustrates, in flow diagram form, a method of using core/shell nanoparticles as imaging agents for computed tomography, in accordance with some embodiments of the present invention.

In some embodiments, the present invention is directed to methods of using any or all of the above-described types of imaging agents in CT applications. Referring to FIG. 3, such methods typically comprise the steps of: (Step 301) providing a quantity of core/shell nanoparticles comprising an active computed tomography contrast agent material, the core/shell nanoparticles each comprising a nanoparticle core and a nanoshell disposed about the nanoparticle core; (Step 302) administering the core/shell nanoparticles to a mammalian subject; and (Step 303) irradiating the subject with X-rays, in accordance with computed tomography, such that the core/shell nanoparticles serve as an imaging agent. In many such embodiments, such core/shell nanoparticles further comprise targeting agents such that, as imaging agents, they can be targeted to specific diseased areas of the subject's body. In some embodiments, the above-described core/shell nanoparticles, to the extent that they persist in the blood, are blood pool agents.

In some such above-described methods of using the above-described imaging agents, the core/shell nanoparticles provide for a CT signal of generally at least about 5 Hounsfield units to at most about 5000 Hounsfield units, and more particularly at least about 100 Hounsfield units to at most about 5000 Hounsfield units.

The following examples are included to demonstrate particular embodiments of the present invention. It should be appreciated by those of skill in the art that the methods disclosed in the examples that follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

EXAMPLE 1

This Example serves to illustrate how a CT imaging agent can be prepared, in accordance with some embodiments of the present invention. In this particular Example, a passive shell is linked to an active core of hafnium oxide.

Figure 4:
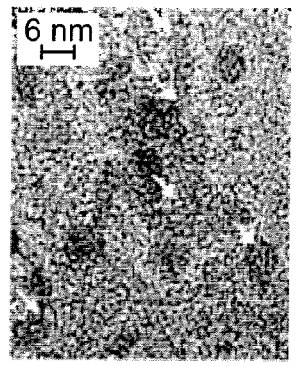
FIG. 4 is a transmission electron microscope (TEM) image of active core/passive shell nanoparticles comprising a hafnium oxide core and polymeric shell, in accordance with some embodiments of the present invention.

Hafnia nanocrystals ($HfO_2$) were prepared from a suspension of hafnium oxychloride in ethanol. An organosilane-based coating was applied as follows: dilute 3-glycidoxypropyl(trimethoxysilane), GPTS was diluted using butanol (volume ratio 1:0.5) and pre-hydrolyzed step by addition of 0.1M HCl keeping the molar ratio of GPTS:$H_2O$ at 1:0.5. The resulting solution was subjected to vigorous stirring overnight at room temperature, then loaded with $HfO_2$ nanocrystals. See Ribeiro et al., Appl. Phys. Lett. 2000, 77 (22), 3502-3504. FIG. 4 is a TEM image of active core/passive shell nanoparticles comprising a hafnium oxide core and polymeric shell, in accordance with some embodiments of the present invention.

EXAMPLE 2

This Example serves to illustrate how a CT imaging agent can be prepared, in accordance with some embodiments of the present invention. In this particular Example, a polymeric passive shell is linked to an active core of tantalum oxide. Further, in this particular Example, the shell formed about the core after the core is formed.

This example illustrates preparation of $Ta_2O_5$ nanoparticles for X-ray imaging: 34 ml of n-propanol, 0.44 ml isobutyric acid and 0.5 ml deuterium oxide were combined under nitrogen in the order specified and stirred for 30 minutes at room temperature. Tantalum ethoxide (1.87 g) was added in a drop-wise manner, albeit rapidly, and stirring continued under nitrogen for 18 hours. The tantalum ethoxide contains Ta(V), that is tantalum in the +5 valence state, a non-zero valence state. 2-[Methoxy(poly-ethylenoxy)propyl]trimethoxysilane (PEGsilane550, 4.832 g) was added to the stirred mixture as a 40 ml solution in n-propanol and the reaction was refluxed for 1 hour in air. Once cooled to room temperature, HCl was added (125 µl, 0.1 M) and the reaction was allowed to stir overnight. Deionized water (40 ml) was added, the mixture stirred, and then all volatiles were removed to obtain a clear, colorless-to-slightly yellow gel-like product. To purify the nanoparticles for intravenous injection, the product was solubilized in deionized water and filtered through a 100 nm membrane. Dialysis in water for 12 hours (3500-8000 MWCO dialysis tubing), followed by 100 nm filtration and subsequent removal of water via lyophilization, yielded an off-white precipitate approximately 22% wt/wt in tantalum. Solutions as high as 1.8 M in tantalum have been prepared using saline (0.9% NaCl).

Figure 5:
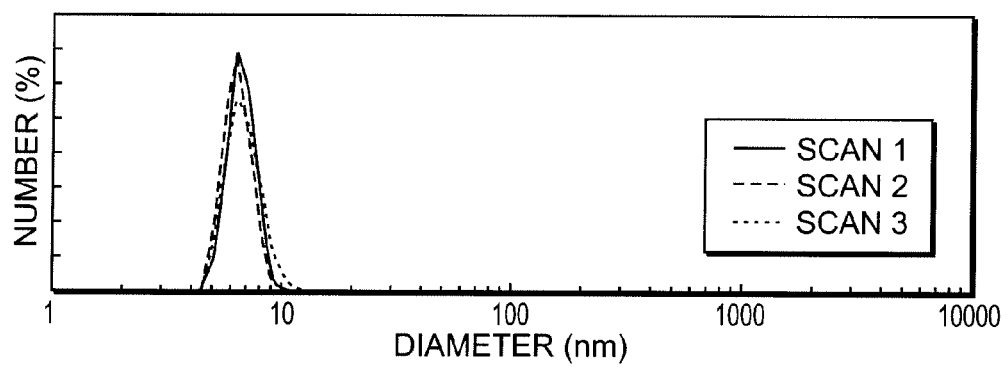
FIG. 5 is a plot of the distribution of diameter of an ensemble of active core/passive shell nanoparticles comprising a tantalum oxide core and a polyethylene glycol (PEG) polymeric shell, in accordance with some embodiments of the present invention.
Figure 6:
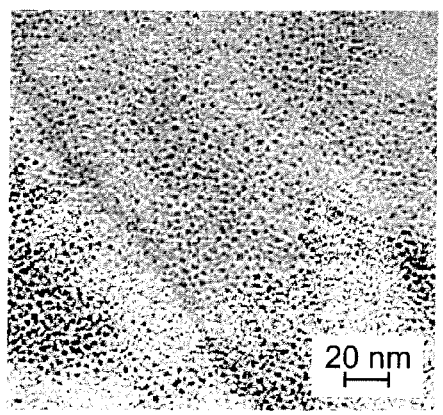
FIG. 6 is a TEM image of active core/passive shell nanoparticles with tantalum oxide and a PEG polymeric shell, in accordance with some embodiments of the present invention.

FIG. 5 shows the distribution of diameters for an ensemble of the nanoparticles made according to this Example, as measured by conventional DLS, demonstrating a mean diameter of the ensemble of 7 nm. FIG. 6 shows a TEM image of nanoparticles made according to this Example.

EXAMPLE 3

This Example serves to illustrate how a CT imaging agent can be prepared, in accordance with some embodiments of the present invention. In this particular Example, a polymeric passive shell is linked to an active core of tantalum oxide. Further, in this particular Example, the shell formed about the core after the core is formed.

This example illustrates preparation of $Ta_2O_5$ nanoparticles for X-ray imaging: 34 ml of n-propanol, 0.44 ml isobutyric acid, and 0.5 ml deuterium oxide were combined under nitrogen in the order specified and stirred for 30 minutes at room temperature. Tantalum ethoxide (1.87 g) was added in a drop-wise manner, albeit rapidly, and stirring continued under nitrogen for 18 hours. The tantalum ethoxide contains Ta(V), that is tantalum in the +5 valence state, a non-zero valence state. Next, diethylphosphatoethyltriethoxysilane (PHS, 3 g) was added to the mixture as a 40 ml solution in n-propanol and the reaction was refluxed for 1.5 hours in air. Once cooled to room temperature, ammonium hydroxide was added (250 µl, 0.1 M) and the reaction was allowed to stir overnight. Deionized water (40 ml) was then added to the reaction with stirring, and then hydrochloric acid was added (10 ml, 1.2 M) and allowed to react for 2 days at 50° C. Upon cooling, the reaction was neutralized with ammonium hydroxide to pH ~7-8 and filtered through a 100 nm membrane. All volatiles were removed to give the product. To purify the nanoparticles for intravenous injection, the product was solubilized in deionized water (pH 7.5-8), filtered through a 100 nm membrane, dialyzed in water for 12 hours (3500-8000 MWCO dialysis tubing), and lyophilized to yield a snow-white precipitate approximately 30% wt/wt in tantalum. IR (nujol mull, NaCl plates, $cm^{-1}$): 1454 (very strong), 1413 (weak), 1376 (strong), 1296 (weak), 1274 (weak), 1218 (strong), 1170 (medium), 1029 (very strong), 964 (very strong), 782 (medium). NMR ($D_2O$, ppm): $^{31}P$, 37.4 (broad); $^{1}H$ (broadened resonances), 4.16, 1.88, 1.37, 0.85.

EXAMPLE 4

This Example serves to illustrate how a CT imaging agent can be prepared, in accordance with some embodiments of the present invention. In this particular Example, a citrate ligand passive shell is linked to an active core of tantalum oxide. Further, in this particular Example, the shell formed in conjunction with the core.

This example describes direct preparation of $Ta_2O_5$ nanoparticles from tantalum powder (325 mesh, Aldrich). The tantalum powder contained Ta(0), that is, tantalum in a zero valence state. A solution was prepared by combination of 20 ml of 30% hydrogen peroxide and 5 ml of ammonium hydroxide solution (28-30% $NH_3$ in water). These were combined in a 2-neck flask under nitrogen and cooled with an ice-bath. Subsequently, the addition of Ta powder (5 mmol, 0.907 g) was made and the mixture was allowed to stir for 2 h (magnetic stirring may be used at small scale, but mechanical stirrer is more appropriate for larger scales). Then citric acid (15 mmol, 3.152 g) was added and a condenser was fitted to the flask. The slurry was heated to 80° C. for 18 h. The reaction was then allowed to cool and the remaining tantalum powder was filtered off through a medium grade glass frit. The filtrate was concentrated by removal of water through rotoevaporation. The remaining colored solution was then dialyzed with a 3.5 K cutoff in an aqueous solution buffered to pH of 7.2. The resulting solution was analyzed for the nanoparticles. If desired, the nanoparticles may be isolated by lyophyllization.

Figure 7:
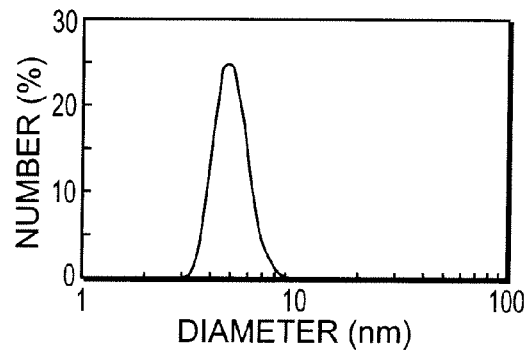
FIG. 7 is a plot of the distribution of diameter of an ensemble of active core/passive shell nanoparticles comprising a tantalum oxide core and a citrate ligand shell, in accordance with some embodiments of the present invention.
Figure 8:
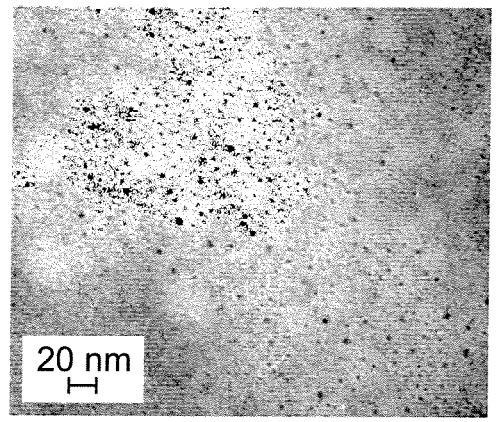
FIG. 8 is a TEM image of active core/passive shell nanoparticles comprising a tantalum oxide core and a citrate ligand shell, in accordance with some embodiments of the present invention.

FIG. 7 shows the distribution of diameters for an ensemble of the nanoparticles made according to this Example as measured by conventional DLS, demonstrating a mean diameter of the ensemble of 7 nm. FIG. 8 shows a TEM image of nanoparticles made according to this Example.

EXAMPLE 5

This Example serves to illustrate how a CT imaging agent can be used, in accordance with some embodiments of the present invention. In this particular Example, cell viability studies of active core/passive shell nanoparticles demonstrate no appreciable loss of cell viability over the studied time period.

THP1 monocytes (ATCC TIB-71) were diluted to final density of $1 \times 10^6$ cells/mL in RPMI 1640+10% FBS media and 500 uL of cells were aliquoted into each well of a 24 well plate. Sterile-filtered tantalum oxide nanoparticles (100 mM Ta) were pipetted into wells. For control wells, either 50 uL of sterile 0.9% saline (negative control) or 80 uL of 30% hydrogen peroxide (positive control) was added to cells. The plate was swirled gently after addition and cells were cultured under normal conditions (37° C., 5% carbon dioxide, 100% humidity).

Following incubation, cells were pipetted into centrifuge tubes and cells were centrifuged at 300×g for 5 minutes at 20 degrees C., and the media was gently aspirated off. The cells were washed with 500 uL of 1×PBS, gently vortexed and centrifuged at 300×g for 5 minutes at 20° C. The cells were washed and the buffer was gently aspirated off. Annexin V FLUOS assay buffer (containing incubation buffer, Annexin V-fluorescein and propidium iodide) was prepared according to manufacturer's protocol (Annexin V FLUOS kit, Roche) and added 100 uL to each tube. Tubes with cells were gently vortexed and incubated at room temperature for 15 minutes. An additional 300 uL of incubation buffer were added to each tube prior to flow cytometry analysis.

The following were measured: the number of cells that were positive for Annexin V-fluorescein alone (apoptotic cells), positive for Annexin V-fluorescein and propidium iodide (necrotic cells) or negative for both (viable cells).

Figure 9:
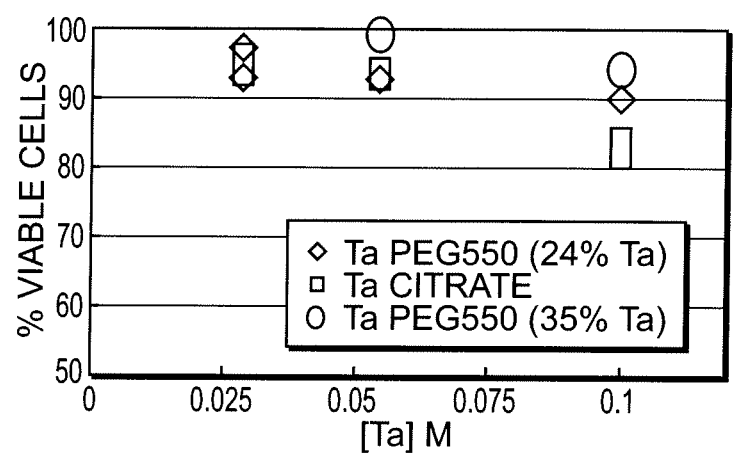
FIG. 9 is a plot of the percentage of viable cells versus molar amount of tantalum for active core/passive shell nanoparticles with a tantalum oxide core and a PEG polymeric shell and for active core/passive shell nanoparticles with a tantalum oxide core and a citrate ligand shell, in accordance with some embodiments of the present invention.

Referring to FIG. 9, all tantalum oxide preparations up to 0.1 mM Ta show negligible number of apoptotic or necrotic cells indicating no loss of cell viability after 3-hour exposure to nanoparticles.

EXAMPLE 6

This Example serves to illustrate how a CT imaging agent can be used, in accordance with some embodiments of the present invention. In this particular Example, complement activation studies of active core/passive shell nanoparticles demonstrate no appreciable increase in C3a compared to untreated or saline-treated serums.

Human plasma and serum was purchased from a commercial vendor (Bioreclamation). To isolate serum, the whole blood was drawn into serum tubes and allowed to clot at room temperature for 30-45 minutes. The sample was centrifuged at 2000×g for 10 minutes and the serum was immediately frozen at −70° C. Samples were shipped overnight on dry ice and stored at −70° C.

Serum was thawed at 37° C. for a few minutes in a water bath. 250 uL of serum was added into individual wells of a 24-well plate. Sterile test samples (Ta agent, saline and cobra venom factor) were added to sera to a final volume of 300 uL. The 24-well plate was transferred to an incubator (37° C.) for 30 minutes with occasional agitation.

Figure 10:
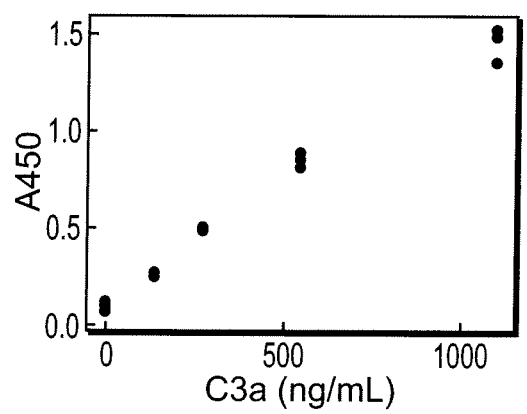
FIG. 10 is a plot of a C3a standard curve to detect C3a in solution in accordance with some embodiments of the present invention.

Referring to FIG. 10, following the manufacturer's protocols (C3a assay, Quidel), stock solutions and dilutions were prepared to generate a C3a standard curve and high/low C3a samples.

To stop C3a production after 30 minute incubation, 37.5 mM sodium citrate was added to each well and 0.5 uL of serum (with and without test samples) was transferred to 1.5 mL of kit sample buffer in Eppendorf tubes. The tubes were inverted 3 times gently to mix the serum and sample buffer, then 100 uL of the diluted serum was added to individual wells of the C3a test strips and incubated at room temperature for 60 minutes. The wells were washed three times with wash buffer (200 uL of wash buffer per wash, wash buffer in the well for 1 minute per wash). 100 uL of C3a conjugate solution was added and the resulting combination incubated for 60 minutes at room temperature. The wash protocol was repeated (three washes, 200 uL of wash buffer per wash, wash buffer in the well for 1 minute per wash) then 100 uL of substrate was added to each well. After incubating 15 minutes, 100 uL of stop solution was added and the absorbance was measured at 450 nm on a 96 well UV plate reader. C3a levels were calculated from C3a standard curve.

Figure 11:
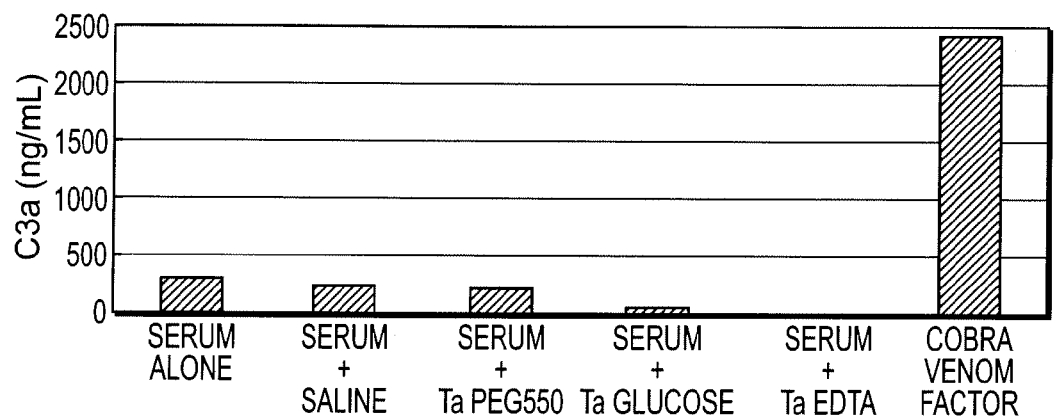
FIG. 11 is a bar chart of C3a for active core/passive shell nanoparticles with a tantalum oxide core and each of the following shells: a glucose shell, an EDTA shell, and PEG shell in accordance with some embodiments of the present invention, and for various controls.

FIG. 11 shows data from analysis. In particular, FIG. 11 shows run data from incubation of tantalum oxide cores with each of the following shells; PEG, EDTA, citrate, and glucose in serum. Though some compounds (Ta EDTA) lowered C3a levels, none showed an increase in C3a compared to either untreated serum or saline-treated serum. No significant increase in C3a levels is observed by addition of up to 100 mM Ta. Elemental analysis via ICP-MS was used to determine total Ta content.

EXAMPLE 7

This Example serves to further illustrate how a core/shell nanoparticle-based CT imaging agent can be used to enhance contrast, in accordance with some embodiments of the present invention.

All imaging studies were performed on a EXplore Locus microCT imaging system using the following parameters: 80 kV, 4 minute acquisition.

A female Dark Agouti rat approximately 160 g in body weight was anesthetized by IP injection of ketamine/diazepam. An IV catheter (24 gage) was placed in the tail vein and flushed with 200 uL of sterile saline. The rat was then imaged on microCT from base of rib cage to bladder (Pre-injection scan). Immediately after the scan, the rat was injected via catheter with 1 mL of 210 mg Ta/mL tantalum oxide-PEG550 agent and scanned following completion of previous scan.

Figure 13:
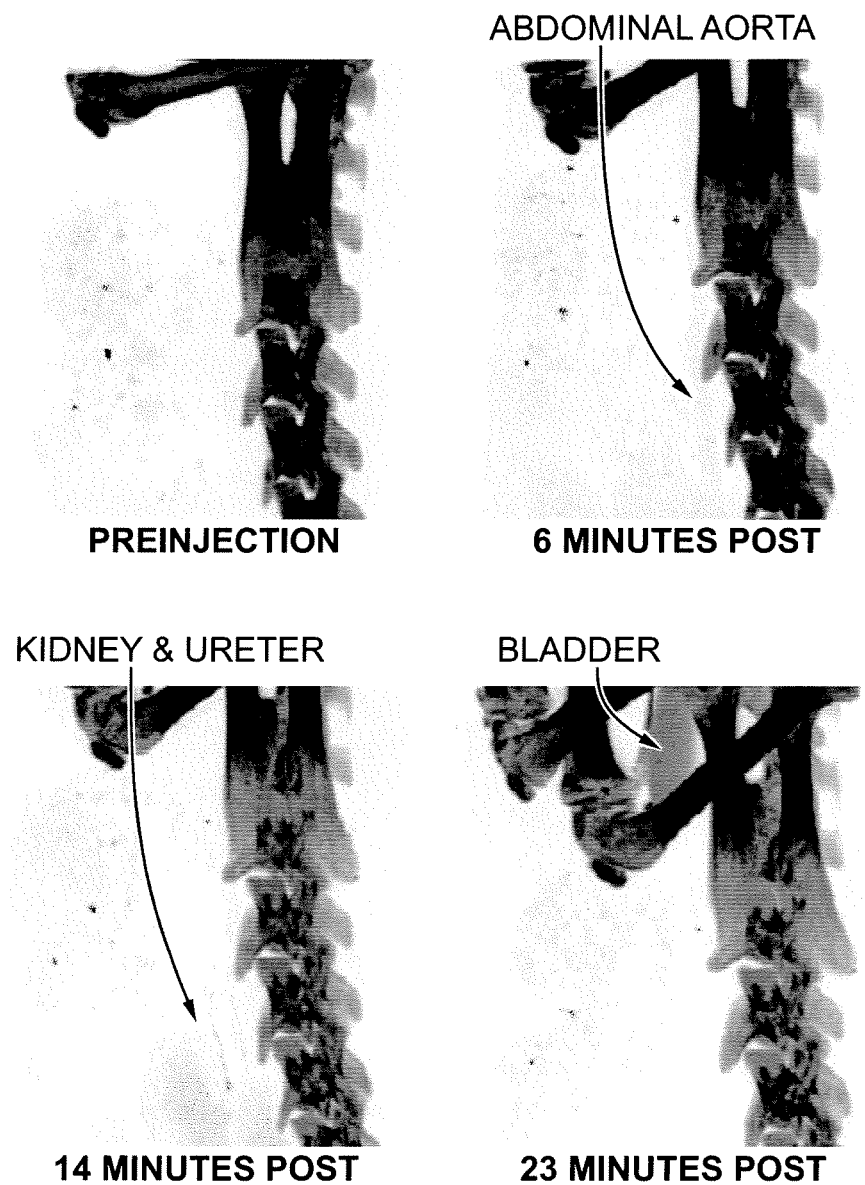
FIG. 13 is a series of computed tomography images at different times of a rat injected with active core/passive shell nanoparticles with a tantalum oxide core and a PEG shell, in accordance with some embodiments of the present invention.

Referring to FIG. 13, images were reconstructed at half resolution and viewed using maximum intensity projections. Immediately following injection, contrast was observed in abdominal aorta, vena cava and renal arteries. Within 14 minutes after injection, the agent was visible in kidney and ureters as it was excreted to bladder. Bladder contrast was prominent within 23 minutes after injection. Still referring to FIG. 13, CT imaging studies show blood clearance between 6-14 minutes, followed by renal excretion to the bladder within 30 minutes.

The rat is imaged for 60 minutes after injection then returned to cage. After 24 hours, the rat is imaged again and no remaining contrast was observed in bladder or kidneys. No adverse effects are observed in injected rats.

Figure 12:
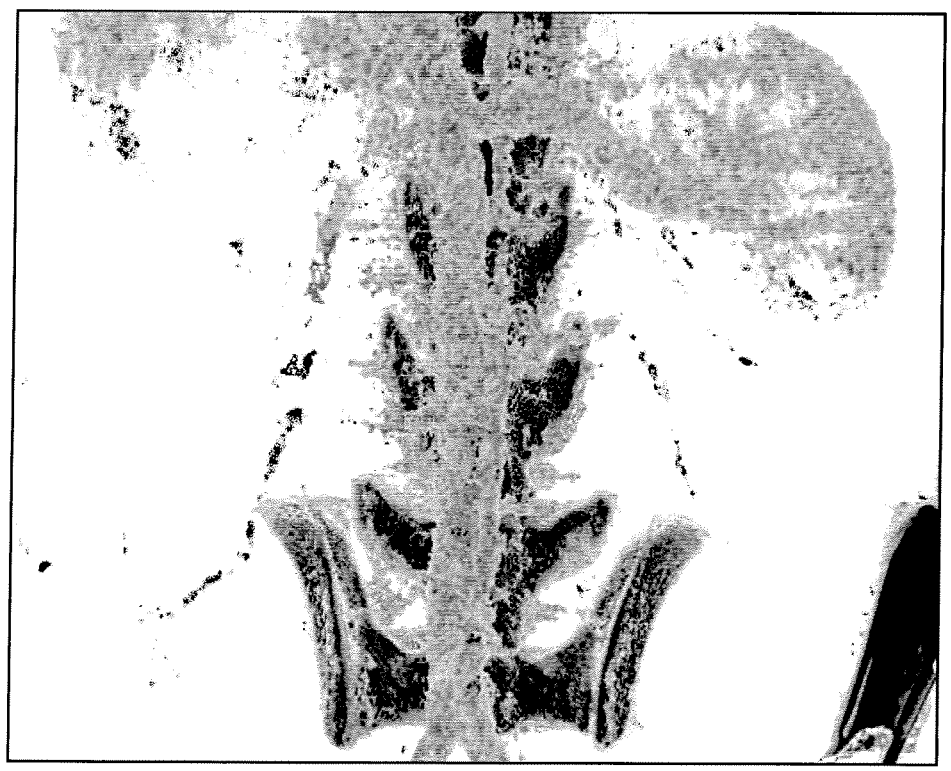
FIG. 12 is a computed tomography image of a rat injected with active core/passive shell nanoparticles with a tantalum oxide core and a PEG shell, in accordance with some embodiments of the present invention.

FIG. 12 shows an abdominal artery image that was obtained by microCT imaging using nanoparticles with $Ta_2O_5$ and PEG shells.

EXAMPLE 8

This Example serves to further illustrate how the mean diameter of an ensemble of core shell nanoparticles can be controlled by filtration, in accordance with some embodiments of the present invention. Further in this example solutions of different particle size were administered into laboratory rat subjects.

Tangential-Flow Filtration (TFF) was employed as a method of removing large tantalum oxide particles, in lieu of using 100 nm or 20 nm membrane filters in Normal Filtration (NF) mode. TFF-compatible molecular weight cut-off (MWCO) filters ranging between 100 kD and 10 kD were used in the TFF process for the purpose of removing larger nanoparticles. Permeates of filters in the specified range (100 kD to 10 kD MWCO) contained smaller tantalum oxide nanoparticles.

TFF was also employed as a method of purifying smaller tantalum oxide nanoparticles in said permeates, by removing low molecular-weight impurities, salts etc. in lieu of dialysis. Molecular-weight cut-off (MWCO) filters ranging between 10 kD and 5 kD were used in the TFF process for the purpose of removing impurities. Retentates of filters in the specified range (10 kD to 5 kD MWCO) contained purified small tantalum oxide nanoparticles.

Moreover, TFF was employed as a process to size-fractionate and purify tantalum oxide nanoparticles in sequential steps. For example, polydisperse tantalum oxide nanoparticles were processed by TFF using a 30 kD MWCO filter thereby retaining ~6 nm particles (retentate) and allowing passage of ~3 nm particles (permeate). Permeates containing ~3 nm particles, then served as retentates in a TFF process employing 10 kD or 5 kD MWCO filters.

TFF is an efficient and scalable process to produce nanoparticles of selected sizes, with a high degree of purity, than achievable by a combination of normal (membrane or centrifugal) filtration and dialysis techniques.

Three preparations of nanoparticle solutions, each having a different nominal mean particle size (20 nm, 6 nm, and 3 nm), were prepared according to the methods described above and administered into laboratory rat subjects at identical dose levels. Twenty four hours after injection, the livers and kidneys of the rats were analyzed to determine concentrations of retained particles (calculated as mgTa/organ-sample). The results indicated that particle clearance from these organs was a strong function of mean particle size. For the kidney, the 6 nm particle concentration was lower than the 20 nm particle concentration by about 20%, and the 3 nm particle concentration was lower than the 20 nm concentration by about 50%. For the liver, the 6 nm particle concentration was lower than the 20 nm particle concentration by about 65% and the 3 nm particle concentration was lower than the 20 nm concentration by about 80%.

It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. In addition, it will be understood, that unless otherwise described, the steps of a method may be performed in any combination and/or order, including, but not limited to simultaneously. It is therefore to be understood that the invention may be practiced otherwise than as specifically described without actually departing from the spirit and scope of the present invention as defined by the appended claims.

What is claimed is:

1. A method for making an injectable solution for use in X-ray/computed tomography, comprising:
   a) providing a first precursor material comprising tantalum;
   b) forming an active core from the first precursor material, the core comprising tantalum in a non-zero valent state;
   c) providing a second precursor material;
   d) forming a passive shell from the second precursor material, wherein the passive shell is disposed about the core such that the core and the shell form a core/shell nanoparticle;
   e) forming a raw ensemble of nanoparticles and fractionating the raw ensemble; wherein fractionating comprises filtering the ensemble; and
   f) preparing the injectable solution of the ensemble nanoparticle in saline;
   wherein the passive shell comprises polyethylene imine, polyvinylsulfate, polyvinylpyrrolidinone, citrate, malate, glycolate, silanes, or combinations thereof; and
   wherein the mean diameter of the ensemble of core/shell nanoparticles is selected so as to render the nanoparticles in the ensemble substantially clearable by a mammalian kidney.

2. The method of claim 1, wherein the mean diameter is less than about 10 nm.

3. The method of claim 1, wherein the mean diameter is less than about 3 nm.

4. The method of claim 1, wherein filtering comprises use of a process selected from the group consisting of tangential flow filtration, diafiltration, and normal flow filtration.

5. The method of claim 1, further comprising purifying the ensemble.

6. The method of claim 5, wherein purifying comprises use of dialysis, tangential flow filtration, or diafiltration.

7. The method of claim 1, wherein the active core comprises tantalum oxide.

8. The method of claim 1, wherein the active core comprises $Ta_2O_5$.

* * * * *